(12) United States Patent
Deckner et al.

(10) Patent No.: US 6,537,537 B2
(45) Date of Patent: Mar. 25, 2003

(54) WATER-IN-SILICONE EMULSION COSMETIC COMPOSITIONS

(75) Inventors: George Endel Deckner, Cincinnati, OH (US); Chune Sang, Middlesex (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/331,803

(22) PCT Filed: Jun. 12, 1998

(86) PCT No.: PCT/US98/12509

§ 371 (c)(1),
(2), (4) Date: Mar. 17, 2000

(87) PCT Pub. No.: WO98/56345

PCT Pub. Date: Dec. 17, 1998

(65) Prior Publication Data

US 2002/0054889 A1 May 9, 2002

(30) Foreign Application Priority Data

Jun. 12, 1997 (GB) .............................................. 9712271

(51) Int. Cl.⁷ ............................................... A61K 9/107
(52) U.S. Cl. ...................... 424/78.02; 424/401; 424/59; 424/60; 514/63; 514/937; 514/938
(58) Field of Search ............................ 424/401, 59, 60, 424/78.02; 514/937, 938, 63

(56) References Cited

U.S. PATENT DOCUMENTS

| 5,302,373 | A |   | 4/1994 | Giacin et al. ................. 424/49 |
| 5,730,969 | A | * | 3/1998 | Hora et al. ................. 424/85.1 |

FOREIGN PATENT DOCUMENTS

| EP | 0 211 392 | 2/1987 | ............ A61K/7/06 |
| EP | 0 352 360 | 1/1990 | ............ A61K/7/42 |
| EP | 0 366 154 | 5/1990 | ............ A61K/7/48 |
| EP | 0 579 435 | 1/1994 | ............ A61K/47/48 |
| EP | 0 803 243 | 10/1997 | ............ A61K/7/16 |
| WO | 92/09307 | 6/1992 | ............ A61K/47/38 |
| WO | 95/31976 | 11/1995 | ............ A61K/9/70 |
| WO | 98/17240 | 4/1998 | ............ A61K/7/32 |

\* cited by examiner

*Primary Examiner*—Raj Bawa
(74) *Attorney, Agent, or Firm*—Kenya T. Pierre; Dara M. Kendall; Tara M. Rosnell

(57) ABSTRACT

Cosmetic composition for topical application to the skin comprise a cyclodextrin compound and a salicylic acid or salicylic acid derivative, wherein the composition is in the form of a water-in-silicone emulsion having a continuous silicone oil-containing phase and a discontinuous aqueous phase.

The compositions herein provide improved anti-acne/anti-inflammatory activity together with reduced skin irritation.

12 Claims, No Drawings

US 6,537,537 B2

WATER-IN-SILICONE EMULSION COSMETIC COMPOSITIONS

This application is a 371 of PCT/US98/12509 filed Jun. 12, 1998.

FIELD OF THE INVENTION

The present invention relates to cosmetic compositions and more particularly, to pigmented foundation make-up compositions and concealers.

BACKGROUND OF THE INVENTION

A foundation composition can be applied to the face and other parts of the body to even skin tone and texture and to hide pores, imperfections, fine lines and the like. A foundation composition is also applied to moisturize the skin, to balance the oil level of the skin and to provide protection against the adverse effects of sunlight, wind and the harsh environment. Make-up compositions are generally available in the form of liquid or cream suspensions, emulsions, gels, pressed powders or anhydrous oil and wax compositions. Such cosmetic make-up compositions are described in U.S. Pat. Nos. 3,444,291, 4,486,405, 4,804,532, 3,978,207, 4,659,562, 5,143,722 and Nakamura et al., Preprints of the XIVth I.F.S.C.C. Congress, Barcelona, 1986, Vol. I, 51–63 (1986).

Foundations in the form of water-in-oil emulsions are well known and provide good coverage and good skin feel, wear and appearance. At the same time, it would be desirable to provide a foundation composition having topical anti-acne activity. It would also be desirable to provide a foundation composition which is mild to the skin and which cause little or no skin irritation. There are many compounds which are known to exhibit anti-acne properties when applied topically to the skin. A commonly used keratolytic agent having anti-acne activity is salicylic acid. As salicylic acid is virtually insoluble in water, it is difficult to incorporate into the aqueous phase of a water-in-oil emulsion. Although salicylic acid can be delivered from the pigment-containing oil phase of a water-in-oil emulsion foundation composition, this can, however, lead to discolouration of the composition due to interaction between the salicylic acid and pigments, especially of the iron oxide type. It would therefore be desirable to deliver the salicylic acid in soluble form from the aqueous phase of a water-in-oil emulsion.

Attempts have been made to improve the solubility of salicylic acid in aqueous phase. One way of doing this involves the use of alcohol solvents such as ethanol. However, such compositions can be harsh and can lead to skin irritation. Another way of helping to solubilise salicylic acid in aqueous systems involves the use of solubilising aids such as PVP. For example, WO 95/04517 discloses a make-up composition in the form of an emulsion comprising an acidic anti-acne active dissolved in the aqueous phase and a pigment or mixture of pigments dispersed in the oil phase. PVP is disclosed as a complexing agent for aiding the solubilisation of salicylic acid. Yet another way of helping to solubilise salicylic acid is by using cyclodextrin compounds. Cyclodextrin compounds are known to form inclusion complexes with salicylic acid which can aid solubilisation in aqueous systems. Ointment type compositions comprising cyclodextrin compounds and salicylic acid are known from the following documents: "Influence of cyclodextrins and other additives of the release of salicylic acid from various ointment bases", Yakuzaigaku, 50(4), 341–346 (1990) and "Effect of additives on release of drugs from ointment bases", Yakuzaigaku, 42(1), 10–16 (1982).

Despite being able to solubilise salicylic acid in the aqueous phases of cosmetic compositions using methods such as described above, there is still a need for cosmetic compositions having improved anti-acne/anti-inflammatory activity together with skin mildness/reduced skin irritation.

It has now been surprisingly found that by incorporating salicylic acid or a salicylic acid derivative and a cyclodextrin compound into a cosmetic composition in the form of a water-in-silicone emulsion having a discontinuous aqueous phase and a silicone-containing continuous phase there is provided a composition having improved anti-acne/anti-bacterial activity together with reduced skin irritation.

It is accordingly a primary object of this invention to provide a cosmetic composition having improved anti-acne activity.

It is also an object of the invention to provide a cosmetic composition having reduced skin irritation.

SUMMARY OF THE INVENTION

In accordance with one aspect of the present invention, there is provided a cosmetic composition comprising salicylic acid or salicylic acid derivative and a cyclodextrin compound wherein the composition is in the form of a water-in-silicone emulsion having a discontinuous aqueous phase and a continuous silicone—containing phase.

The cosmetic compositions of the present invention provide improved anti-acne/anti-inflammatory activity, mildness and reduced skin irritation.

All levels and ratios are by weight of total composition, unless otherwise indicated. Chain lengths and degrees of alkoxylation are also specified on a weight average basis.

DETAILED DESCRIPTION OF THE INVENTION

The cosmetic composition according to the present invention comprises a cyclodextrin compound and salicylic acid or salicylic acid derivative.

Cyclodextrin Compound

The first essential ingredient of the cosmetic compositions herein is a cyclodextrin compounds. As used herein, the term "cyclodextrin" (CD) includes unsubstituted cyclodextrins containing from six to twelve glucose units, especially, alpha-, beta-, gamma-, cyclodextrins, and/or derivatives thereof, and mixtures thereof, that are capable of forming inclusion complexes with salicylic acid or salicylic acid derivatives.

There are many derivatives of cyclodextrins that are known. Representative derivatives are those disclosed in U.S. Pat. No. 3,426,011, Parmerter et al., issued Feb. 4, 1969; U.S. Pat. Nos. 3,453,257, 3,453,258, 3,453,259, 3,453,260, all in the names of Parmerter et al., and all issued Jul. 1, 1969; U.S. Pat. No. 3,459,731, Gramera et al., issued Aug. 5, 1969; U.S. Pat. No. 2,553,191, Parmerter et al., issued Jan. 5. 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,638,058, Brandt et al., issued Jan. 20, 1987; U.S. Pat. No. 4,746,734, Tsuchiyama et al., issued May 24, 1988; and U.S. Pat. No. 4,678,598, Ogino et al., issued Jul. 7, 1987, all of said patents being incoroporated herein by reference. Examples of cyclodextrin derivatives suitable for use herein are methyl-beta-cyclodextrin, hydroxyethyl-beta-cyclodextrin, and hydroxypropyl-beta-cyclodextrin of different degrees of substitution (DS).

The individual cyclodextrins can also be linked together, for example, using multifunctional agents to form oligomers, polymers, etc. An example of such a material is beta-cyclodextrin/epichlorohydrin copolymers.

It is also suitable to use mixtures of cyclodextrins to provide a mixture of complexes. Mixtures of cyclodextrins can conveniently be obtained by using intermediate products from known processes for the preparation of cyclodextrins including those processes described in U.S. Pat. No. 3,425,910, Armbruster et al., issued Feb. 4, 1969; U.S. Pat. No. 3,812,011, Okada et al., issued May 21, 1974; U.S. Pat. No. 4,317,881, Yagi et al., issued Mar. 2, 1982; U.S. Pat. No. 4,418,144, Okada et al., issued Nov. 29, 1983; and U.S. Pat. No. 4,738,923, Ammeraal, issued Apr. 19, 1988, all of said patents being incorporated herein by reference.

Preferred cyclodextrin compounds for use in the compositions herein are hydroxy(C1–C4)alkyl-cyclodextrins, especially hydroxypropyl-beta-cyclodextrin.

The cyclodextrin compound is present in the cosmetic compositions of the present invention at a level of from about 0.1% to about 20%, preferably from about 0.8% to about 15%, especially from about 4% to about 12%, by weight of the composition.

A second essential component of the compositions herein is salicylic acid or salicylic acid derivative. The term salicylic acid derivative as used herein means any 2,3 or 4-OR substituted benzoic acid compound having the formula:

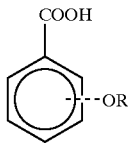

wherein R is selected from $C_1$–$C_6$ alkyl or $C_1$–$C_6$ acyl, preferably wherein R is selected from $C_2$–$C_3$ alkyl or $C_2$–$C_3$ acyl. Especially preferred herein is salicylic acid.

The salicylic acid or salicylic acid derivative is present in an amount which is safe and effective for providing anti-acne/anti-inflammatory activity, and preferably at a level of from about 0.1% to about 10%, more preferably from about 0.1% to about 5%, and especially from about 0.5% to about 2%, by weight of composition.

As used herein, "safe and effective amount" means a sufficient amount of a compound, composition or other material described by this phrase to significantly induce a positive modification in the condition being treated, but low enough to avoid undue side effects (e.g., significant skin irritation or sensitization), within the scope of sound judgement of the skilled person. The safe and effective amount of the compound, composition or other material may vary with the particular skin being treated, the age and physical condition of the biological subject being treated, the severity of the condition, the duration of treatment, the nature of concurrent therapy, the specific compound, composition, or other material employed, the particular cosmetically acceptable topical carrier utilized, and the factors within the knowledge and expertise of the skilled person.

Water-in-silicone Emulsion

The cosmetic compositions of the present invention are in the form of a water-in-silicone emulsion having a silicone oil-containing continuous phase and an aqueous discontinuous phase.

The emulsion compositions herein preferably comprises from about 20% to about 95%, more preferably from about 30% to about 70% by weight of silicone oil-containing phase, and from about 5% to about 80%, more preferably from about 30% to about 70% by weight of aqueous phase. The aqueous phase preferably comprises from about 40% to about 90%, more preferably from about 60% to about 80% by weight of aqueous phase of water. The total level of water in the compositions herein is in the range of from about 10% to about 60%, more preferably from about 30% to about 50% by weight of composition.

Silicone Oil-containing Phase

The composition comprises a continuous silicone oil-containing phase.

In preferred embodiments the silicone oil-containing phase comprises a mixture of volatile silicones and non-volatile silicones. The silicones are useful herein for providing skin conditioning properties. The silicone fluid is present in an amount of from about 1% to about 50% by weight. Suitable volatile silicones include cyclic and linear volatile polyorganosiloxanes. The term "nonvolatile" as used herein shall mean the material has a vapour pressure of no more than 0.1 mm Hg at one atmosphere and 25° C. The term "volatile" as used herein shall mean materials which are not nonvolatile or which have a vapour pressure at the same conditions of more than 0.1 mm Hg.

A description of various volatile silicones is found in Todd, et al. "Volatile Silicone Fluids for Cosmetics", 91 Cosmetics and Toiletries 27–32 (1976).

Preferred cyclic silicones include cyclic dimethyl siloxane chains containing an average of from about 3 to about 9 silicon atoms, preferably from about 4 to about 5 silicon atoms. Preferred linear silicones include the polydimethylsiloxanes containing an average of from about 3 to about 9 silicon atoms. The linear volatile silicones generally have viscosities of less than about 5 centistokes at 25° C., while the cyclic materials have viscosities of less than about 10 centistokes. Examples of silicone oils useful in the present invention include: Dow Corning 344, Dow Corning 245, Dow Corning 345, and Dow Corning 200 (manufactured by the Dow Corning Corporation): Silicone 7207 and Silicone 7158 (manufactured by the Union Carbide Corporation). SF:202 (manufactured by General Electric) and SWS-03314 (manufactured by Stauffer Chemical).

The nonvolatile silicones will have vapour pressures as previously defined, and preferably will have an average viscosity of from about 10 to about 100,000 cps at 25° C., more preferably from about 100 to about 10,000 cps, even more preferably from about 500 to about 6000 cps. Lower viscosity non-volatile silicone conditioning agents, however, can also be used. Viscosity can be measured-by means of a glass capillary viscometer as set forth in Dow Coming Corporate Test Method CTM0004, Jul. 20, 1970.

Suitable non-volatile silicone fluids for use herein include polyalkyl siloxanes, polyaryl siloxanes, polyalkylaryl siloxanes, polysiloxanes with amino functional substitutions, polyether siloxane copolymers, and mixtures thereof. The siloxanes useful in the present invention may be substituted and/or endcapped with any number of moieties, so long as the material remains suitable for use in a topical cosmetic product, including, for example, methyl, hydroxyl, ethylene oxide, propylene oxide, amino and carboxyl. However, other silicone fluids having skin conditioning properties may be used. The non-volatile polyalkyl siloxane fluids that may be used include, for example, polydimethylsiloxanes. These siloxanes are available, for example, from the General Electric Company as a Viscasil (RTM) series and from Dow Corning as the Dow Corning 200 series. Preferably, the viscosity ranges from about 10 $mm^2.s^{-1}$ to about 100,000 $mm^2.s^{-1}$ at 25° C. The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid. The polyether siloxane copolymer that may be used includes, for example, a polypropylene oxide modified dimethylpolysiloxane (e.g., Dow Corning DC-1248) although ethylene oxide or mixtures of ethylene oxide and propylene oxide may also be used.

References disclosing suitable silicone fluids include U.S. Pat. No. 2,826,551, Green; U.S. Pat. No. 3,964,500, Drakoff, issued Jun. 22nd, 1976; U.S. Pat. No. 4,364,837, Pader; and GB-A-849,433, Woolston. In addition, Silicone Compounds distributed by Petrarch Systems Inc., 1984 provides an extensive (though not exclusive) listing of suitable silicone fluids.

Preferred non-volatile silicones for use herein include polydiorganosiloxane-polyoxyalkylene copolymers containing at least one polydiorganosiloxane segment and at least one polyoxyalkylene segment. The polydiorganosiloxane segment has the general formula:

$$R_bSiO_{(4-b)/2}$$

siloxane units wherein b has a value of from about 0 to about 3, inclusive, there being an average value of approximately two R radicals per silicon for all siloxane units in the copolymer, and R denotes a radical selected from methyl, ethyl, vinyl, phenyl and a divalent radical bonding said polyoxyalkylene segment to the polydiorganosiloxane segment. The polyoxyalkylene segment has an average molecular weight of at least about 500, preferably at least about 1000, and comprising from about 0 to about 50 mol percent polyoxypropylene units and from about 50 to about 100 mol percent polyoxyethylene units, at least one terminal portion of said polyoxyalkylene segment being grafted to, or covalently bonded directly or indirectly to a polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer preferably having a value of from about 2 to about 8. Such polymers are described in U.S. Pat. No. 4,268,499.

Preferred for use herein are polydiorganosiloxane-polyoxyalkylene copolymers having the general formula:

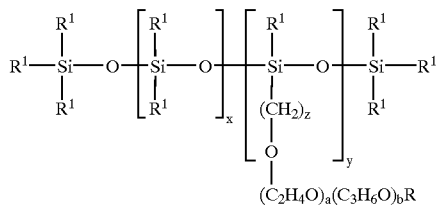

wherein $R^1$ is selected from C1 to C5 alkyl groups, preferably methyl, z is in the range of from 1 to 4, x and y are selected such that the weight ratio of polydiorganosiloxane segments to polyoxalkylene segments is from about 2 to about 8, the mol ratio of a:(a+b) is from about 0.5 to about 1, and R is a chain terminating group, especially selected from hydrogen; hydroxyl; alkyl, such as methyl, ethyl, propyl, butyl, benzyl; aryl, such as phenyl; alkoxy such as methoxy, ethoxy, propoxy, butoxy; benzyloxy; aryloxy, such as phenoxy; alkenyloxy, such as vinyloxy and allyloxy; acyloxy, such as acetoxy, acryloxy and propionoxy and amino, such as dimethylamino.

More preferred for use herein are polydiorganosiloxane-polyoxyalkylene copolymers having the formula:

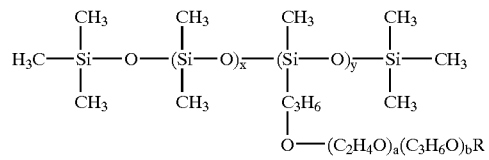

wherein x, y and R are as defined above.

The number of and average molecular weights of the segments in the copolymer are such that the weight ratio of polydiorganosiloxane segments to polyoxyalkylene segments in the copolymer is preferably from about 2.5 to about 4.0.

Suitable copolymers are available commercially under the tradenames Belsil (RTM) from Wacker-Chemie GmbH, Geschaftsbereich S, Postfach D-8000 Munich 22 and Abil (RTM) from Th. Goldschmidt Ltd,. Tego House, Victoria Road, Ruislip, Middlesex, HA4 0YL. Particularly preferred for use herein are Belsil (RTM) 6031, Abil (RTM) B88183, DC3225C, DC5200, Abil We09, Abil EM90, BY22-008 (Dow Corning) and SF1328 (GE Silicones). A preferred silicone herein is known by its CTFA designation as dimethicone copolyol.

The compositions of the present invention preferably comprise from about 20% to about 95% by weight of composition of silicone oil-containing phase. The silicone-oil containing phase preferably comprises from about 0.01% to about 25%, more preferably from about 0.05% to about 10% by weight of the silicone oil-containing phase of non-volatile silicones. The silicone oil-containing phase preferably comprises from about 75% to about 99.99%, more preferably from about 90% to about 99.95% by weight of the silicone oil-containing phase of volatile silicones.

The silicone oil-containing phase in the water-in-silicone emulsions of the present invention can also comprise one or more non-silicone organic oil, such as natural or synthetic oil selected from mineral, vegetable, and animal oils, fats and waxes, fatty acid esters, fatty alcohols, fatty acids and mixtures thereof, which ingredients are useful for achieving emollient cosmetic properties. It will be understood that the silicone oil-containing phase may contain, for example, up to about 25%, preferably up to only about 10% of oil phase soluble emulsifier ingredients. Such ingredients are not to be considered as oil phase components from the viewpoint of determining the oil phase level.

Suitable organic oils for use herein include, for example, optionally hydroxy-substituted $C_8$–$C_{50}$ unsaturated fatty acids and esters thereof, $C_1$–$C_{24}$ esters of $C_8$–$C_{30}$ saturated fatty acids such as isopropyl myristate, isopropyl palmitate, cetyl palmitate and octyldodecylmyristate (Wickenol 142), beeswax, saturated and unsaturated fatty alcohols such as behenyl alcohol and cetyl alcohol, hydrocarbons such as mineral oils, petrolatum and squalane, fatty sorbitan esters (see U.S. Pat. No. 3,988,255, Seiden, issued Oct. 26, 1976), lanolin and lanolin derivatives, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, shea butter, shorea butter, and sunflower seed oil and $C_1$–$C_{24}$ esters of dimer and trimer acids such as diisopropyl dimerate, diisostearylmalate, diisostearyldimerate and triisostearyltrimerate. Of the above, highly preferred are the mineral oils, petrolatums, unsaturated fatty acids and esters thereof and mixtures thereof.

Optional Ingredients

A wide variety of optional ingredients can be incorporated into the compositions. The following are non-limiting examples of numerous ingredients that can be used.

Acidic Skin Care Active

The compositions of the present invention can comprise an acidic skin care active, in addition to salicylic acid or salicylic acid derivative.

Suitable acidic skin care actives can be selected from hydroxycarboxylic acids. As used herein the term acidic skin care active means any skin care active containing an acidic functional group (e.g. carboxy, sulfonic).

Suitable hydroxycarboxylic acids can be selected from hydroxymonocarboxylic acids having the following chemical structure:

$$R_1(CR_2OH)_m(CH_2)_n COOH$$

wherein $R_1$, $R_2$=H, alkyl, aralkyl or aryl group of saturated or unsaturated, straight or branched chain or cyclic form, having from 1 to 25 carbon atoms; m=1,2,3,4,5,6,7,8 or 9; n=0 or a numerical number up to 23.

The hydroxymonocarboxylic acid may be present as a free acid, lactone, or salt form, The lactone form could be either inter or intramolecular lactone, however, most common ones are intramolecular lactones with a ring structure formed by elimination of one or more water molecules between a hydroxy group and the carboxylic group. Since the hydroxymonocarboxylic acids are organic in nature, they may form a salt or a complex with an inorganic or organic base such as ammonium hydroxide, sodium or potassium hydroxide, or triethanolamine.

The hydroxymonocarboxylic acid and its related compounds may exist as stereoisomers such as D, L, and DL forms.

Typical alkyl, aralkyl and aryl groups for $R_1$ and $R_2$ include methyl, ethyl, propyl, isopropyl, benzyl and phenyl. The hydrogen atoms of the $R_1$ and $R_2$ and $(CH_2)n$ may be substituted by a nonfunctional element such as F, Cl, Br, I, S or a radical such as a lower alkyl or alkoxy, saturated or unsaturated, having 1 to 9 carbon atoms. Representative hydroxymonocarboxylic acids are 2-hydroxyacetic acid (glycolic acid), 2-hydroxypropanoic acid (lactic acid), 2-methyl 2-hydroxypropanoic acid (methyllactic acid), 2-hydroxybutanoic acid, phenyl 2-hydroxyacetic acid (mandelic acid), phenyl 2-methyl 2-hydroxyacetic acid, 3-phenyl 2-hydroxypropanoic acid (phenyllactic acid), 2,3-dihydroxypropanoic acid (glyceric acid), 2.3.4-trihydroxybutanoic acid, 2,3,4,5-tetrahydroxypentanoic acid, 2,3,4,5,6-pentahydroxyhexanoic acid, 2-hydroxydodecanoic acid (alpha hydroxylauric acid), 2,3, 4,5,6,7-hexahydroxyheptanoic acid, diphenyl 2-hydroxyacetic acid (benzilic acid), 4-hydroxymandelic acid, 4-chloromandelic acid, 3-hydroxybutanoic acid, 4-hydroxybutanoic acid, 2-hydroxyhexanoic acid, 5-hydroxydodecanoic acid, 12-hydroxydodecanoic acid, 10-hydroxydecanoic acid, 16-hydroxyhexadecanoic acid, 2-hydroxy-3-methylbutanoic acid, 2-hydroxy-4-methylpentanoic acid, 3-hydroxy-4-methoxymandelic acid, 4-hydroxy-3-methoxymendelic acid, 2-hydroxy-2-methylbutanoic acid, 3-(2-hydroxyphenyl) lactic acid, 3-(4-hydroxyphenyl) lactic acid, hexahydromandelic acid, 3-hydroxy-3-methylpentanoic acid, 4-hydroxydecanoic acid, 5-hydroxydecanoic acid and aleuritic acid.

Another type of hydroxyacid suitable for use herein is a hydroxydicarboxylic acid having the following formula:

$$HOOC(CHOH)_m(CH_2)_n COOH$$

wherein m=1,2,3,4,5,6,7,8 or 9; n=0 or an integer up to 23.

The hydroxydicarboxylic acid may also be present as a free acid, lactone or salt form. The hydroxydicarboxylic acid and its related compounds may also exist as stereoisomers such as D, L, DL and meso forms.

The hydrogen attached to the carbon atom may be substituted by a nonfunctional element such as F, Cl, Br, I, S, or a radical such as a lower saturated or unsaturated alkyl or alkoxy having from 1 to 9 carbon atoms.

Representative hydroxydicarboxylic acids are 2-hydroxypropanedioic acid (tartronic acid), 2-hydroxybutanedioic acid (malic acid), erythraric acid and threaric acid (tartaric acid), arabiraric acid, ribaric acid, xylaric acid and lyxaric acid, glucaric acid (saccharic acid), galactaric acid (mucic acid), mannaric acid, gularic acid, allaric acid, altraric acid, idaric acid and talaric acid.

A third type of hydroxyacid suitable for use herein is a miscellaneous group of compounds which is not readily represented by the above generic structure of either the first type or the second type described above. Included in the third type of hydroxyacids are the following:

Hydroxycarboxylic acids of formula:

$$R(OH)_m(COOH)_n$$

wherein m, n=1,2,3,4,5,6,7,8 or 9, R=H, alkyl, aralkyl or aryl group of saturated or unsaturated, straight or branched chain or cyclic form, having from 1 to 25 carbon atoms; citric acid, isocitric acid, citramalic acid, agaricic acid (n-hexadecylcitric acid), quinic acid, uronic acids including glucuronic acid, glucuronolactone, galacturonic acid, galacturonolactone, hydroxypyruvic acid, hydroxypyruvic acid phosphate, ascorbic acid, dihydroascorbic acid, dihydroxytartaric acid, 2-hydroxy-2-methylbutanoic acid, 1-hydroxy-1-cyclopropane carboxylic acid, 2-hydroxyhexanedial, 5-hydroxylysine, 3-hydroxy-2-aminopentanoic acid, tropic acid, 4-hydroxy-2,2-diphenylbutanoic acid, 3-hydroxy-3-methylglutaric acid and 4-hydroxy-3-pentenoic acid.

The third type of hydroxyacid may also be present as a free acid, lactone or salt form and may also exist as stereoisomers such as D, L, DL and meso forms.

The hydrogen atom attached to the carbon atom may be substituted by a nonfunctional element such as F, Cl, Br, I, S or a radical such as a lower saturated or unsaturated alkyl or alkoxy having from 1 to 9 carbon atoms.

Mixtures of hydroxy acids can also be used in the compositions herein. Hydroxy acids are useful herein from the viewpoint of reducing wrinkles and improving skin feel and appearance.

Other suitable hydroxy acids for use herein include retinoic acid, and azelaic acid.

The acidic skin care active can be present at a level of from about 0.1% to about 10%, preferably from about 0.1% to about 5%, more preferably from about 0.5% to about 3%, by weight of composition.

The acidic skin care active can be solubilized in water or a hydroalcoholic solution, for example, solutions based upon $C_2$–$C_6$ alcohols, diols and polyols, preferred alcohols being selected from ethanol, dipropylene glycol, butylene glycol, hexylene glycol, and mixtures thereof.

The compositions of the present invention can also comprise a solubilizing agent, in addition to the cyclodextrin compound, for solubilizing the acidic skin care active and/or salicylic acid or salicylic acid derivative. Any solublizing agent suitable for use in a cosmetic composition can be used. Preferably the solubilizing agent herein is selected from polyoxyethylene-polyoxypropylene ethers of C4 to C22 alcohols, pyrrolidone-based solubilising agents, polyethylene glycol based nonionic surfactants having an HLB of greater than about 15, preferably greater than about 18, and mixtures thereof.

Pyrrolidone-based solubilising agents suitable for use herein include polyvinylpyrrolidone or $C_1$–$C_4$ alkyl polyvinylpyrrolidone having a molecular weight (viscosity average) in the range from about 1500 to about 1,500,000, preferably from about 3000 to about 700,000, more preferably from about 5000 to about 100,000. Suitable examples of pyrrolidone-based solubilising agents are polyvinylpyrrolidone (PVP) (or povidone) and butylated polyvinylpyrrolidone. The most preferred pyrrolidone-based solubilising agent herein is polyvinylpyrrolidone. PVP is commercially available under the trade name Luviskol (RTM) from BASF. A preferred PVP solubilising agent herein is Luviskol K17 which has a viscosity-average molecular weight of about 9,000. Other pyrrolidone-based solubilising agents for use herein include $C_1$–$C_{18}$ alkyl or hydroxyalkyl pyrrolidones such as lauryl pyrrolidone.

The pyrrolidone-based solubilising agent is preferably present in the composition herein in a level of from about 0.1% to about 10%, more preferably from about 0.1% to about 5%, especially from about 0.5% to about 2% by weight of composition.

Preferred embodiments of the invention additionally comprise from about 0.01% to about 5% by weight of an additional acid or salt thereof which is soluble in water at pH values of less than or equal to the $pK_a$ of the corresponding acid, for example, an acid selected from citric acid, boric acid, and salts, and mixtures thereof. These materials are valuable herein in combination with the pyrrolidone-based complexing agent from the viewpoint of aiding solubilization of the acidic skin care active/salicylic acid or salicylic acid derivative. Particularly preferred herein from this viewpoint is a sodium salt of citric acid. In preferred embodiments, the acid or salt thereof is soluble to a level of at least 5% w/w at 25° C.

A particularly preferred solubilizing agent in the compositions of the present invention is a nonionic surfactant selected from polyoxyethylene-polyoxypropylene ethers of C4–C22 alcohols, and mixtures thereof. The nonionic surfactant is valuable herein as a solubilising agent for the acidic skin care active in the discontinuous aqueous phase. Suitable polyoxyethylene-polyoxypropylene ethers of C4–C22 alcohols for use herein include those having the general formula:

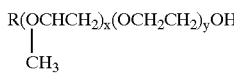

wherein x is in the range of from about 1 to about 35, preferably from about 1 to about 10, y is in the range of from about 1 to about 45, preferably from about 1 to about 30 and R is a straight chain or branched chain C4 to C22 alkyl group, or a mixture thereof. In preferred embodiments (x+y) is greater than or equal to 5, preferably greater than or equal 10, more preferably greater than or equal to 15. The ratio of x:y is in the range from 1:1 to 1:10.

Examples of suitable R groups in the above formula include cetyl, butyl, stearyl, cetearyl, decyl, lauryl and myristyl.

Examples of suitable polyoxyethylene-polyoxypropylene alcohol ethers include (using CTFA designations) PPG-4-Ceteth-1, PPG-4-Ceteth-5, PPG-4-Ceteth-10, PPG-4-Ceteth-20, PPG-5-Ceteth-20, PPG-8-Ceteth-1, PPG-8-Ceteth-2, PPG-8-Ceteth-5, PPG-8-Ceteth-10, PPG-8-Ceteth-20, PPG-2-Buteth-3, PPG-2-Buteth-5, PPG-5-Buteth-7, PPG-9-Buteth-12, PPG-28-Buteth-35, PPG-12-Buteth-16, PPG-15-Buteth-20, PPG-20-Buteth-30, PPG-24-Buteth-27, PPG-26-Buteth-26, PPG-33-Buteth-45, PPG-2-Ceteareth-9, PPG-4-Ceteareth-12, PPG-10-Ceteareth-20, PPG-2-Deceth-10, PPG-4-Deceth-4, PPG-6-Deceth-4, PPG-6-Deceth-9, PPG-8-Deceth-6, PPG-2-Isodeceth-4, PPG-2-Isodeceth-6, PPG-2-Isodeceth-9, PPG-2-Isodeceth-12, PPG-3-Isodeceth-1, PPG-4-Laureth-5, PPG-4-Laureth-2, PPG-4-Laureth-7, PPG-5-Laureth-5, PPG-25-Laureth-25, PPG-3-Myreth-11, PPG-3-Myreth-3 and PPG-9-Steareth-3.

Preferred polyoxyethylene-polyoxypropylene ethers for use herein are ethers of C8 to C16 alcohols having the formula (I) wherein x is from 2 to 12 and y is from 10 to 30 and where the ratio of x:y is in the range of from about 1:2 to about 1:8.

Particularly preferred polyoxyethylene-polyoxypropylene ethers of C4 to C22 alcohols for use herein are those having the formula (I) above wherein R is cetyl and wherein x is in the range of from about 4 to about 8, and wherein y is in the range of from about 15 to about 25, and the ratio of x:y is in the range of from about 1:3 to about 1:5. A particularly preferred ether from the viewpoint of improving solubilisation of the acidic skin care active is PPG-5-Ceteth-20, which is available under the tradename Procetyl AWS.

The solubilizing agent herein is preferably present at a level of from about 0.1% to about 15%, more preferably from about 1% to about 10%, especially from about 2% to about 8% by weight of composition.

Preferred embodiments herein comprise a pigment or mixture of pigments. The pigment used herein must be compatible with any acidic skin care active/salicylic acid/salicylic acid derivative which is present in the composition and have excellent overall colour stability. Suitable pigments for use herein can be inorganic and/or organic. Also included within the term pigment are materials having a low colour or luster such as matte finishing agents, and also light scattering agents. Examples of suitable pigments are iron oxides, rutile titanium dioxide, anatase titanium dioxide, ferric oxide, ferrous oxide, chromium oxide, chromium hydroxide, manganese violet, acylglutamate iron oxides, ultramarine blue, D&C dyes, carmine, and mixtures thereof. Depending upon the type of make-up composition, eg. foundation or blusher, a mixture of pigments will normally be used.

The foundation composition can also include at least one matte finishing agent. The function of the matte finishing agent is to hide skin defects and reduce shine. Such cosmetically acceptable inorganic agents, i.e., those included in the CTFA Cosmetic Ingredient Dictionary, Third Ed., as silica, hydrated silica, silicone-treated silica beads, mica, talc, polyethylene, titanium dioxide, bentonite, hectorite, kaolin, chalk, diatomaceous earth, attapulgite zinc oxide and the like may be utilized. Of particular usefulness as a matte finishing agent is low luster pigment such as titanated mica (mica coated with titanium dioxide) coated with barium sulfate. Of the inorganic components useful as a matte finishing agent low luster pigment, talc, polyethylene, hydrated silica, kaolin, titanium dioxide and mixtures thereof are particularly preferred. Materials suitable for use herein as light-scattering agents can be generally described as spherical shaped inorganic materials having a particle size of up to about 100 microns, preferably from about 5 to about 50 microns, for example spherical silica particles.

Other examples of pigments include lakes of organic colorants such as FD&C Red No. 7 calcium lake, FD&C Yellow No. 5 aluminium lake, D&C Red No. 9 barium lake, and D&C Red No. 30.

The preferred pigments for use herein from the viewpoint of moisturisation, skin feel, skin appearance and emulsion compatibility are treated pigments. The pigments can be treated with compounds such as amino acids such as lysine, silicones, lauroyl, collagen, polyethylene, lecithin and ester oils. The more preferred pigments are the silicone (polysiloxane) treated pigments.

A highly preferred pigment for use herein is a pigment which has been coated with organosilicon component selected from a polyorganosiloxane or a silane wherein the coated pigment has a hydrogen potential of less than about 2.0, preferably less than about 1.0, more preferably less than about 0.5 ml, and especially less than about 0.1 ml $H_2$/g of coated pigment. The pigment preferred for use herein is in particulate form. The pigment is incorporated into the continuous oil phase in the compositions herein. The coatings used can be bonded to the pigment surface by covalent bonding, physical adsorption or adhesion, preferably by covalent bonding to the surface of the pigment. The function of the coatings herein is to hydrophobically-modify the pigments so that thay are "wettable" in the continuous silicone phase of the water-in-silicone emulsions. The coated pigment is also useful herein from the viewpoint of reducing hydrogen gas evolution and improving product stability.

Without wishing to be limited by theory it is believed that although the pigments are present in the oil phase of the water-in-oil emulsion, hydrogen ions from the aqueous phase can pass through the interface of the emulsion into the oil phase, where they are available to react with the pigment coatings, e.g. to give off hydrogen gas. However, by using organosilicon-coated pigments having a hydrogen potential of less than about 2 ml $H_2$/g of coated pigment, hydrogen gas generation is reduced.

The hydrogen potential of the coated pigment is measured herein using the following test method:

A dispersion of the coated pigment containing 20 g of coated pigment is placed in a flask on a magnetic stirrer and 100 ml of a 2% ethanolic solution of potassium hydroxide is added with stirring at ambient temperature. The hydrogen gas which is evolved is collected in a second flask at ambient temperature and pressure (25° C., 1At). The hydrogen gas released can therefore be volumetrically measured.

A wide variety of organosilicon components can be used for treating the pigments herein. A suitable polyorganosiloxane herein is selected from:

(A) material of the formula:

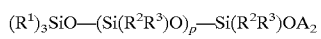

wherein p is 1 to 1000, preferably from 1 to 100, $A_2$ is hydrogen or an alkyl group having from 1 to 30 carbon atoms, $R^1$ is a $C_1$–$C_{30}$ alkyl, preferably methyl, $R^2$ and $R^3$ are independently selected from a $C_1$–$C_{30}$ alkyl and a phenyl, preferably wherein $R^2$ and $R^3$ are both methyl or wherein $R^2$ is methyl and $R^3$ is phenyl; or (B) material of the formula:

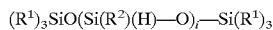

wherein i is 1 to 1000, preferably 1 to 100, and wherein $R^1$ and $R^2$ are as defined above for formula (A).

In preferred embodiments the organosilicon component is selected from a silane. The silane can be selected from material of the formula:

(C) 

wherein A is an alkyl or alkenyl group having from 1 to 30 carbon atoms, and $X_1$, $X_2$ and $X_3$ are independently $C_1$–$C_4$ alkoxy preferably methoxy or ethoxy, or halo, preferably chloro.

When the pigment herein is treated with silane material having the formula (C) described herein above a pigment having the following formula (1) is produced:

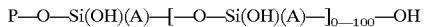

wherein P is an atom in the pigment surface and each A is an alkyl or alkenyl group having up to 30 carbon atoms. A number of adjacent polysiloxane chains as shown in formula (1) can be cross-linked through oxygen atoms to form a polysiloxane chain with up to 100 repeating —Si(—OP)—O— units that extend along the pigment surface, in addition to the polysiloxane chain which extends away from the pigment surface. Examples of linear or branched alkyl groups are methyl, ethyl, propyl, butyl, pentyl, hexyl, heptyl, octyl, and so forth up to octadecyl. "Alkenyl" includes carbon chains with one or more double bonds; examples of such groups include ethylene, propylene, acrylyl, methacrylyl, and residues of unsaturated fatty acids such as oleic ($C_{17}C_{33}$—), linoleic ($C_{17}H_{31}$—), and linolenic ($C_{17}H_{29}$—).

When the pigment herein is treated with polyorganosiloxane material having the formula (A) described hereinabove a pigment having the following formula (2) is produced:

 (2)

wherein p is 1–1000, preferably 1 to 100, $R^1$, $R^2$ and $R^3$ are as defined above for formula (A) and P is an atom in the pigment surface.

When the pigment herein is treated with polyorganosiloxane material having the formula (B) described hereinabove a pigment having the following formula (3) is produced:

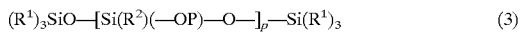 (3)

wherein each P is an atom in the pigment surface, p is from 1 to 1000, preferably from 1 to 100, $R^1$ and $R^2$ are as defined above in formula (B) and in which each of the up to 100 repeating (Si—O) units is bonded through an oxygen atom to the pigment surface.

The pigment (or a mixture of two or more pigments) can be coated by placing it in dry, finely divided form in a mixer, adding the organosilicon component, and mixing. The organosilicon coating is preferably present at a level of from about 0.01% to about 5%, more preferably from about 0.1% to about 4%, and especially from about 0.5% to about 2%, by weight of the organosilicon coated pigment.

The most preferred coated pigment from the viewpoint of reducing hydrogen gas evolution and improving product stability is Cardre 70429.

The total concentration of the coated pigment may be from about 0.1 to about 25% by weight and is preferably from about 1 to about 15%, more preferably from about 8% to about 12% by weight of the total composition, the exact concentration being dependent to some extent upon the specific mixture of pigments selected for use in a foundation make-up or blusher to achieve the desired shades. The preferred compositions contain from about 2% to about 20% by weight of titanium dioxide and most preferably from about 5% to about 10% by weight of titanium dioxide.

A highly preferred component of the compositions herein is a humectant or mixture of humectants. The humectant or mixture of humectants herein is present in an amount of from about 0.1% to about 30% preferably from about 1% to about 25%, and more preferably from about 1% to about 10% by weight of composition. Suitable humectants are selected from glycerine and polyglycerylmethacrylate lubricant having a viscosity at 25° C. of 300,000 to 1,100,000 cps; a specific gravity at 25° C. of 1 to 1.2 g/ml, a pH of 5.0 to 5.5; a bound water content of 33 to 58%; and, a free water content from 5 to 20%.

The humectant can be incorporated at least partly into the oil phase of a water-in-oil emulsion. The oil phase preferably comprises from about 0.1% to about 10%, more preferably from about 0.1% to about 3% by weight of humectant on a composition basis. The humectant can be introduced into the oil phase in the form of a mixture with or incorporated within a particulate lipophilic or hydrophobic carrier material.

Polyglycerylmethacrylate lubricants having the desired properties are marketed by Guardian Chemical Corporation under the trademark "Lubrajel". The "Lubrajels" identified as "Lubrajel DV", "Lubrajel MS", and "Lubrajel CG" are preferred in the present invention. The gelling agents sold under these trademarks contain about 1% propylene glycol.

Other suitable humectants include sorbitol, panthenols, propylene glycol, dipropylene glycol, butylene glycol, hexylene glycol, alkoxylated glucose derivatives, such as Glucam (RTM) E-20, hexanetriol, and glucose ethers, and mixtures thereof.

The panthenol moisturiser can be selected from D-panthenol ([R]-2,4-dihydroxy-N-[3-hydroxypropyl)]-3,3-dimethylbutamide), DL-panthenol, calcium pantothenate, royal jelly, panthetine, pantotheine, panthenyl ethyl ether, pangamic acid, pyridoxin, pantoyl lactose and Vitamin B complex.

The preferred humectant herein is glycerine. Chemically, glycerine is 1,2,3-propanetriol and is a product of commerce.

A preferred component of the compositions herein, in addition to the organic amphiphilic surfactant is a polyol ester skin conditioning agent.

The compositions of the present invention preferably comprise from about 0.01% to about 20%, more preferably from about 0.1% to about 15%, and especially from about 1% to about 10% by weight of the polyol ester. The level of polyol ester by weight of the oil in the composition is preferably from about 1% to about 30%, more preferably from about 5% to about 20%.

The polyol ester preferred for use herein is a nonocclusive liquid or liquifiable polyol carboxylic acid ester. These polyol esters are derived from a polyol radical or moiety and one or more carboxylic acid radicals or moieties. In other words, these esters contain a moiety derived from a polyol and one or more moieties derived from a carboxylic acid. These carboxylic acid esters can also be derived from a carboxylic acid. These carboxylic acid esters can also be described as liquid polyol fatty acid esters, because the terms carboxylic acid and fatty acid are often used interchangeably by those skilled in the art.

The preferred liquid polyol polyesters employed in this invention comprise certain polyols, especially sugars or sugar alcohols, esterified with at least four fatty acid groups.

Accordingly, the polyol starting material must have at least four esterifiable hydroxyl groups. Examples of preferred polyols are sugars, including monosaccharaides and disaccharides, and sugar alcohols. Examples of monosaccharides containing four hydroxyl groups are xylose and arabinose and the sugar alcohol derived from xylose, which has five hydroxyl groups, i.e., xylitol. The monosaccharide, erythrose, is not suitable in the practice of this invention since it only contains three hydroxyl groups, but the sugar alcohol derived from erythrose, i.e., erythritol, contains four hydroxyl groups and accordingly can be used. Suitable five hydroxyl group-containing monosaccharides are galactose, fructose, and sorbose. Sugar alcohols containing six —OH groups derived from the hydrolysis products of sucrose, as well as glucose and sorbose, e.g., sorbitol, are also suitable. Examples of disaccharide polyols which can be used include maltose, lactose, and sucrose, all of which contain eight hydroxyl groups.

Preferred polyols for preparing the polyesters for use in the present invention are selected from the group consisting of erythritol, xylitol, sorbitol, glucose, and sucrose. Sucrose is especially preferred.

The polyol starting material having at least four hydroxyl groups is esterified on at least four of the —OH groups with a fatty acid containing from about 8 to about 22 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids; they can be saturated or unsaturated, including positional and geometrical isomers. However, in order to provide liquid polyesters preferred for use herein, at least about 50% by weight of the fatty acid incorporated into the polyester molecule should be unsaturated. Oleic and linoleic acids, and mixtures thereof, are especially preferred.

The polyol fatty acid polyesters useful in this invention should contain at least four fatty acid ester groups. It is not necessary that all of the hydroxyl groups of the polyol be esterified with fatty acid, but it is preferable that the polyester contain no more than two unesterified hydroxyl groups. Most preferably, substantially all of the hydroxyl groups of the polyol are esterified with fatty acid, i.e., the polyol moiety is substantially completely esterified. The fatty acids esterified to the polyol molecule can be the same or mixed, but as noted above, a substantial amount of the unsaturated acid ester groups must be present to provide liquidity.

To illustrate the above points, a sucrose fatty triester would not be suitable for use herein because it does not contain the required four fatty acid ester groups. A sucrose tetra-fatty acid ester would be suitable, but is not preferred because it has more than two unesterified hydroxyl groups. A sucrose hexa-fatty acid ester would be preferred because it has no more than two unesterified hydroxyl groups. Highly preferred compounds in which all the hydroxyl groups are esterified with fatty acids include the liquid sucrose octa-substituted fatty acid esters.

The following are non-limiting examples of specific polyol fatty acid polyesters containing at least four fatty acid ester groups suitable for use in the present invention: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof.

As noted above, highly preferred polyol fatty acid esters are those wherein the fatty acids contain from about 14 to about 18 carbon atoms.

The preferred liquid polyol polyesters preferred for use herein have complete melting points below about 30° C., preferably below about 27.50° C., more preferably below about 25° C. Complete melting points reported herein are measured by Differential Scanning Calorimetry (DSC).

The polyol fatty acid polyesters suitable for use herein can be prepared by a variety of methods well known to those skilled in the art. These methods include: transesterification of the polyol with methyl, ethyl or glycerol fatty acid esters using a variety of catalysts; acylation of the polyol with a fatty acid chloride; acylation of the polyol with a fatty acid anhydride; and acylation of the polyol with a fatty acid, per se. See U.S. Pat. Nos. 2,831,854; 4,005,196, to Jandacek, issued Jan. 25, 1977; U.S. Pat. No. 4,005,196, to Jandacek, issued Jan. 25, 1977.

The make-up compositions of the present invention can also comprise a particulate cross-linked hydrophobic acrylate or methacrylate copolymer. This copolymer is particularly valuable for reducing shine and controlling oil while helping to provide effective moisturization benefits. The cross-linked hydrophobic polymer is preferably in the form of a copolymer lattice with at least one active ingredient dispersed uniformly throughout and entrapped within the copolymer lattice. Alternatively, the hydrophobic polymer can take the form of a porous particle having a surface area ($N_2$-BET) in the range from about 50 to 500, preferably 100 to 300 $m^2/g$ and having the active ingredient absorbed therein.

The cross-linked hydrophobic polymer when used herein is in an amount of from about 0.1% to about 10% by weight and is preferably incorporated in the external silicone-containing oil phase. The active ingredient can be one or more or a mixture of skin compatible oils, skin compatible humectants, emollients, moisturizing agents and sunscreens. The polymer material is in the form of a powder, the powder being a combined system of particles. The system of powder particles forms a lattice which includes unit particles of less than about one micron in average diameter, agglomerates of fused unit particles of sizes in the range of about 20 to 100 microns in average diameter and aggregates of clusters of fused agglomerates of sizes in the range of about 200 to 1,200 microns in average diameter.

The powder material of the present invention which can be employed as the carrier for the active ingredient can be broadly described as a cross-linked "post absorbed" hydrophobic polymer lattice. The powder preferably has entrapped and dispersed therein, an active which may be in the form of a solid, liquid or gas. The lattice is in particulate form and constitutes free flowing discrete solid particles when loaded with the active material. The lattice may contain a predetermined quantity of the active material. The polymer has the structural formula:

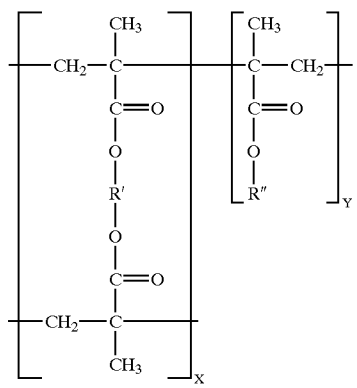

where the ratio of x to y is 80:20, R' is —$CH_2CH_2$— and R" is —$(CH_2)_{11}CH_3$.

A suitable hydrophobic polymer for use herein is a highly crosslinked polymer, more particularly a highly cross-linked polymethacrylate copolymer such as that manufactured by the Dow Corning Corporation, Midland, Mich., USA, and sold under the trademark POLYTRAP (RTM). It is an ultralight free-flowing white powder and the particles are capable of absorbing high levels of lipophilic liquids and some hydrophilic liquids while at the same time maintaining a free-flowing powder character. The powder structure consists of a lattice of unit particles less than one micron that are fused into agglomerates of 20 to 100 microns and the agglomerates are loosely clustered into macro-particles or aggregates of about 200 to about 1200 micron size. The polymer powder is capable of containing as much as four times its weight of fluids, emulsions, dispersions or melted solids.

Adsorption of actives onto the polymer powder can be accomplished using a stainless steel mixing bowl and a spoon, wherein the active is added to the powder and the spoon is used to gently fold the active into the polymer powder. Low viscosity fluids may be adsorbed by addition of the fluids to a sealable vessel containing the polymer and then tumbling the materials until a consistency is achieved. More elaborate blending equipment such as ribbon or twin cone blenders can also be employed. The preferred active ingredient for use herein is glycerine. Preferably, the weight ratio of humectant: carrier is from about 1:4 to about 3:1.

Also suitable as a highly cross-linked polymethacrylate copolymer is Microsponges 5640. This takes the form of generally spherical particles of cross-linked hydrophobic polymer having a pore size of from about 0.01 to about 0.05 μm and a surface area of 200–300 $m^2/g$. Again, it is preferably loaded with humectant in the levels described above.

The compositions of the invention can also contain a hydrophilic gelling agent at a level preferably from about 0.01% to about 10%, more preferably from about 0.02% to about 2%, and especially from about 0.02% to about 0.5%. The gelling agent preferably has a viscosity (1% aqueous solution, 20° C., Brookfield RVT) of at least about 4000 mPa.s, more preferably at least about 10,000 mPa.s and especially at least 50,000 mPa.s.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), polyvinylalcohol, polyquaternium-10, guar gum, hydroxypropyl guar gum and xanthan gum.

Among suitable hydrophilic gelling agents are acrylic acid/alkyl acrylate copolymers and the carboxyvinyl polymers sold by the B. F. Goodrich Company under the trade mark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are hydrophobically-modified cross-linked polymers of acrylic acid having amphipathic properties available under the Trade Name Carbopol 1382, Carbopol 1342 and Pemulen TR-1 (CTFA Designation: Acrylates/10-30 Alkyl Acrylate Crosspolymer). A combination of the polyalkenyl polyether cross-linked acrylic acid polymer and the hydrophobically modified cross-linked acrylic acid polymer is also suitable for use herein. Other suitable gelling agents suitable for use herein are oleogels such as trihydroxystearin and aluminium magnesium hydroxy stearate. The gelling agents herein are particularly valuable for providing excellent stability characteristics over both normal and elevated temperatures.

Preferably the acidic group containing hydrophilic gelling agents are neutralized. Neutralizing agents suitable for use in neutralizing acidic group containing hydrophilic gelling agents herein include sodium hydroxide, potassium hydroxide, ammonium hydroxide, monoethanolamine, diethanolamine and triethanolamine.

The make-up compositions herein can additionally comprise an emollient. Emollients suitable for the compositions of the present invention include natural and synthetic oils selected from mineral, vegetable, and animal oils, fats and waxes, fatty acid esters, fatty alcohols, alkylene glycol and polyalkylene glycol ethers and esters, fatty acids and mixtures thereof.

Suitable emollients for use herein include, for example, optionally hydroxy-substituted $C_8$–$C_{50}$ unsaturated fatty acids and esters thereof, $C_1$–$C_{24}$ esters of $C_8$–$C_{30}$ saturated fatty acids such as isopropyl myristate, cetyl palmitate and octyldodecylmyristate (Wickenol 142), beeswax, saturated and unsaturated fatty alcohols such as behenyl alcohol and cetyl alcohol, hydrocarbons such as mineral oils, petrolatum and squalane, fatty sorbitan esters (see U.S. Pat. No. 3,988,255, Seiden, issued Oct. 26, 1976), lanolin and lanolin derivatives, such as lanolin alcohol ethoxylated, hydroxylated and acetylated lanolins, cholesterol and derivatives thereof, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil and $C_1$–$C_{24}$ esters of dimer and trimer acids such as diisopropyl dimerate, diisostearylmalate, diisostearyldimerate and triisostearyltrimerate.

Preferred emollients are selected from hydrocarbons such as isohexadecane, mineral oils, petrolatum and squalane, lanolin alcohol, and stearyl alcohol. These emollients may be used independently or in mixtures and may be present in the composition of the present invention in an amount from about 1% to about 30% by weight, and preferably are present in an amount from about 5% to about 15% by weight of the total composition.

The composition may also contain additional materials such as, for example, fragrances, sun-screens, preservatives, electrolytes such as sodium chloride, proteins, antioxidants, chelating agents and water-in-oil emulsifiers as appropriate.

Another optional component of the make-up composition is one or more ultraviolet absorbing agents. Ultraviolet absorbing agents, often described as sunscreening agents, can be present in a concentration in the range of between about 1% and about 12% by weight, based on the total weight of composition. Preferably, the UV absorbing agents constitute between about 2% and 8% by weight. More preferably, the UV absorbing agents can be present in the composition in a concentration range of between about 4% and about 6% by weight. Of the ultraviolet absorbing agents suitable for use herein, benzophenone-3, octyl dimethyl PABA (Padimate O), Parsol MCX, and mixtures thereof are particularly preferred.

Another optional but preferred component herein is one or more additional chelating agents, preferably in the range of from about 0.02% to about 0.10% by weight, based on the total weight of the composition. Preferably, the chelating agent is present in a concentration in the range of between about 0.03% and about 0.07% by weight, based on the total weight of the composition. Among the chelating agents that may be included in the composition is tetrasodium EDTA.

Another optional but preferred component of the foundation composition is one or more preservatives. The preservative concentration in the foundation composition, based on the total weight of that composition, is in the range of between about 0.05% and about 0.8% by weight, preferably between about 0.1% and about 0.3% by weight. Suitable preservatives for use herein include sodium benzoate and propyl paraben, and mixtures thereof.

Another optional but preferred component is DryFlow supplied by Dow Corning Ltd, Avco House, Castle Street, Reading RG17DZ, UK.

The cosmetic compositions of the present invention can be in the form of foundations, blushers, concealers, compact powders, moisturising creams and lotions, tinted moisturising creams and lotions, and the like, preferably as foundations and concealers.

The table below shows examples of cosmetic compositions of the present invention.

|  | 1 (%, w/w) | 2 (%, w/w) | 3 (%, w/w) | 4 (%, w/w) | 5 (%, w/w) | 6 (%, w/w) | 7 (%, w/w) | 8 (%, w/w) |
|---|---|---|---|---|---|---|---|---|
| Phase A | | | | | | | | |
| Cyclomethicone (DC 2-1330) | 0.0 | 0.0 | 7.59 | 16.75 | 5.25 | 11.99 | 0.0 | 0.0 |
| Cyclomethicone DC 245 | 9.85 | 8.65 | 0.0 | 0.0 | 0.0 | 0.0 | 10.04 | 10.04 |
| Cyclomethicone/Dimethicone Copolyol (90:10) (DC 3225C) | 0.0 | 0.0 | 17.20 | 10.00 | 18.50 | 10.00 | 0.0 | 0.0 |

-continued

|  | 1 (%, w/w) | 2 (%, w/w) | 3 (%, w/w) | 4 (%, w/w) | 5 (%, w/w) | 6 (%, w/w) | 7 (%, w/w) | 8 (%, w/w) |
|---|---|---|---|---|---|---|---|---|
| Cyclomethicone/Dimethicone Copolyol (90:10) (BY22-008) | 10.00 | 15.00 | 0.0 | 0.0 | 0.0 | 0.0 | 15.00 | 15.00 |
| SEFA Cottonate[1] | 0.00 | 0.00 | 2.00 | 0.00 | 2.00 | 4.00 | 0.00 | 0.00 |
| Phase B | | | | | | | | |
| Microsponge 5640[2] | 0.5 | 0.75 | 0.75 | 0.00 | 0.50 | 0.75 | 0.75 | 0.75 |
| Mica | 0.00 | 0.00 | 0.00 | 0.10 | 0.10 | 0.10 | 0.00 | 0.00 |
| Titanium Dioxide (Cardre 70429)[3] | 8.25 | 8.25 | 8.25 | 8.25 | 8.25 | 8.25 | 8.25 | 8.25 |
| Zinc Oxide & Dimethicone | 0.00 | 0.00 | 4.00 | 4.00 | 0.00 | 4.00 | 0.00 | 0.00 |
| Phase C | | | | | | | | |
| Dryflow[4] | 2.5 | 2.50 | 0.00 | 0.00 | 0.00 | 0.00 | 2.5 | 2.5 |
| Phase D | | | | | | | | |
| Yellow Iron Oxide | 2.10 | 2.10 | 2.00 | 2.10 | 2.10 | 2.10 | 1.60 | 1.60 |
| Red Iron Oxide | 0.90 | 0.90 | 0.24 | 0.90 | 0.60 | 0.90 | 0.47 | 0.47 |
| Black Iron oxide | 0.60 | 0.60 | 0.12 | 0.60 | 0.30 | 0.60 | 0.09 | 0.09 |
| Cyclomethicone (DC 2-1330) | 0.0 | 0.0 | 1.00 | 1.00 | 1.00 | 1.00 | 0.0 | 0.0 |
| Cyclomethicone DC 245 | 1.00 | 1.00 | 0.0 | 0.0 | 0.0 | 0.0 | 1.00 | 1.00 |
| Phase E | | | | | | | | |
| Durachem[5] | 0.00 | 0.00 | 0.00 | 0.00 | 0.00 | 0.00 | 0.00 | 0.00 |
| Waxenol[6] | 0.00 | 0.00 | 0.30 | 0.00 | 0.00 | 0.00 | 0.00 | 0.00 |
| Phase F | | | | | | | | |
| Cyclomethicone (DC 2-1330) | 0.0 | 0.0 | 1.00 | 1.00 | 1.00 | 1.00 | 0.0 | 0.0 |
| Cyclomethicone DC 245 | 1.00 | 1.00 | 0.0 | 0.0 | 0.0 | 0.0 | 1.00 | 1.00 |
| Thixin R[7] | 0.30 | 0.30 | 0.30 | 0.30 | 0.30 | 0.30 | 0.30 | 0.30 |
| Propyl Paraben | 0.00 | 0.00 | 0.25 | 0.00 | 0.00 | 0.00 | 0.00 | 0.00 |
| Phase G | | | | | | | | |
| Ethylene Brassylate | 0.00 | 0.00 | 0.00 | 0.00 | 0.10 | 0.00 | 0.00 | 0.00 |
| Phase H | | | | | | | | |
| Salicylic Acid | 1.00 | 0.5 | 1.75 | 1.95 | 1.50 | 1.50 | 1.00 | 1.50 |
| Hydroxy propyl β cyclodextrin[10] | 8.00 | 4.00 | 8.00 | 8.00 | 12.00 | 8.00 | 4.00 | 8.00 |
| Procetyl AWS[11] | 0.00 | 0.00 | 0.00 | 0.00 | 0.00 | 0.00 | 3.00 | 3.00 |
| Glycerine | 6.00 | 6.00 | 6.00 | 6.00 | 6.00 | 6.00 | 6.00 | 6.00 |
| Water | 2.00 | 2.00 | 2.00 | 2.00 | 2.00 | 2.00 | 0.00 | 0.00 |
| Phase I | | | | | | | | |
| Water | | | | To 100 | | | | |
| Na4EDTA | 0.10 | 0.10 | 0.10 | 0.10 | 0.10 | 0.10 | 0.10 | 0.10 |
| Sodium Citrate | 0.30 | 0.30 | 0.30 | 0.30 | 0.30 | 0.30 | 0.30 | 0.30 |
| Sodium Chloride | 0.30 | 0.30 | 0.30 | 0.30 | 0.30 | 0.30 | 0.30 | 0.30 |
| Citric Acid | 0.5 | 1.00 | 0.00 | 0.00 | 0.50 | 0.00 | 0.50 | 0.50 |
| Polyvinylpyrrolidone (Luviskol K17)[8] | 1.00 | 1.00 | 1.00 | 1.00 | 1.00 | 1.00 | 1.00 | 1.00 |
| Methyl Paraben | 0.00 | 0.00 | 0.20 | 0.00 | 0.00 | 0.00 | 0.00 | 0.00 |
| Phase J | | | | | | | | |
| Zinc Oxide | 0.00 | 0.00 | 0.42 | 0.42 | 0.00 | 0.28 | 0.00 | 0.00 |
| Arginine[12] | 0.00 | 0.00 | 0.325 | 0.65 | 0.65 | 0.65 | 0.00 | 0.00 |
| Total: | 100 | 100 | 100 | 100 | 100 | 100 | 100 | 100 |

[1]Supplied by Procter & Gamble
[2]Supplied by Dow Corning Ltd, Avco House, Castle Street, Reading RG1 7DZ, UK
[3]Supplied by Cardre Incorporated, 70 Tyler Pl., South Plainfield, NJ 07090, USA
[4]Supplied by Dow Corning Ltd, Avco House, Castle Street, Reading RG1 7DZ, UK
[5]Supplied by Astor-Stag Ltd., Tavistock Road, Wets Drayton, Middlesex UB7 7RA, UK
[6]Supplied by Caschem Inc., 40 Avenue A, Bayonne, NJ 07002, USA
[7]Trihydroxystearin, supplied by Rheox Ltd, Barons Court, Manchester Road, Wilmslow, SK9 1BQ, UK
[8]Supplied by BASF, Earl Road, Cheadle Hulme, Cheadle, Cheshire, SK8 6QB
[9]Supplied by Union Carbide, 39 Old Ridgebury Road, Danbury
[10]Supplied by Cerestar USA Inc., 1100 Indianapolis Boulevard, Hammond, Indiana, USA 46320
[11]Supplied by Croda Chemicals Ltd., Cowick Hall, Snaith, Goole, North Humberside, DN14 9AA
[12]Supplied by Degussa Ltd, Winterton House, Winterton Way, Macclesfield, Cheshire SK11 0LP The formulations of Examples I to VI can be prepared as follows. The various components listed in the Table have been segregated into groups, the constituents of each group being mixed together before being added to members of the remaining groups in accordance with the procedures set forth below.

In the first step, the mixture of components of phase A is stirred for approximately 15 minutes with shear mixing until homogeneous. With high speed shear mixing, the materials of phase B are added gradually to A and the batch is mixed for about 30 minutes. Phase C is added and the resulting mixture is ground for approximately 15 minutes.

The components from phase D are then added and the resulting mixture is ground until fully dispersed.

The waxy phase E is then added to the batch and the batch is heated to 85° C. with mixing until the waxes have melted and then cooled to 50° C. with stirring. Phase F premix is then added to the batch and homogenised for 10 minutes. The batch is cooled to room temperature with stirring. Phase G is added to the batch and homogenised for 10 minutes.

The water phase is prepared as follows. The components of phase I are mixed until dissolved. The components of phase H are mixed together under high speed shear until dissolved. The solution is mixed until clear. Phase I is added to phase H and mixed, followed by addition of phase J under mixing.

The water phase is finally added to the oil phase slowly whilst homogenising at a low speed, with stirring. When all of the water phase has been added, high shear is applied to the batch for approximately 5 minutes to increase the viscosity of the final product.

The resulting make-up composition is ready for packaging.

The cosmetic compositions of the Examples exhibit improved anti-acne/anti-inflammatory activity and reduced skin irritation.

What is claimed is:

1. Cosmetic composition for topical application to the skin comprising a cyclodextrin compound selected from the group consisting of alpha-cyclodextrin, beta-cyclodextrin, gamma-cyclodextrin, hydroxyalkyl-beta-cyclodextrin, and mixtures thereof and a salicylic acid or salicylic acid derivative, wherein the composition is in the form of a water-in-silicone emulsion having a continuous silicone-containing phase and a discontinuous aqueous phase.

2. Cosmetic composition according to claim 1 wherein the cyclodextrin compound is hydroxypropyl-beta-cyclodextrin.

3. Cosmetic composition according to claim 1 comprising salicylic acid.

4. Cosmetic composition according to claim 3 comprising from about 0.1% to about 10%, by weight, of salicylic acid or salicylic acid derivative.

5. Cosmetic composition according to claim 2 comprising from about 0.1% to about 20%, by weight, of cyclodextrin compound.

6. Cosmetic composition according to claim 4 wherein the salicylic acid or salicylic acid derivative is solubilised in the aqueous phase.

7. Cosmetic composition according to claim 1 additionally comprising from about 0.1% to about 30%, by weight, of pigment.

8. Cosmetic composition according to claim 1 wherein the silicone oil phase comprises from about 0.01% to about 25%, by weight of the silicone oil phase, of non-volatile silicones and from about 75% to about 99.99%, by weight of the silicone oil phase, of volatile silicones.

9. Cosmetic composition according to claim 4 comprising from about 0.1% to about 5%, by weight, of salicylic acid or salicylic acid derivative.

10. Cosmetic composition according to claim 5 comprising from about 0.8% to about 15%, by weight, of cyclodextrin compound.

11. Cosmetic composition according to claim 7 additionally comprising from about 0.1% to about 25%, by weight, of pigment.

12. Cosmetic composition according to claim 11 additionally comprising from about 1% to about 15%, by weight, of pigment.

* * * * *